United States Patent
Koob et al.

(10) Patent No.: US 9,463,206 B2
(45) Date of Patent: *Oct. 11, 2016

(54) CROSS-LINKED DEHYDRATED PLACENTAL TISSUE GRAFTS AND METHODS FOR MAKING AND USING THE SAME

(71) Applicant: MiMedx Group, Inc., Kennesaw, GA (US)

(72) Inventors: Tom Koob, Santa Fe, NM (US); John Daniel, Kennesaw, GA (US); Randall Spencer, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,150

(22) Filed: Dec. 18, 2012

(65) Prior Publication Data

US 2013/0202676 A1 Aug. 8, 2013

Related U.S. Application Data

(60) Provisional application No. 61/579,206, filed on Dec. 22, 2011.

(51) Int. Cl.
| | |
|---|---|
| A61K 35/50 | (2015.01) |
| A61L 27/36 | (2006.01) |
| A61L 27/60 | (2006.01) |
| A61L 15/40 | (2006.01) |
| A61L 27/50 | (2006.01) |

(52) U.S. Cl.
CPC ............. *A61K 35/50* (2013.01); *A61L 15/40* (2013.01); *A61L 27/3604* (2013.01); *A61L 27/3687* (2013.01); *A61L 27/50* (2013.01); *A61L 27/60* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 2,694,914 A | 11/1954 | Glover, Jr | |
| 4,361,552 A | 11/1982 | Baur, Jr. | |
| 4,564,368 A | 1/1986 | Sawyer et al. | |
| 4,745,771 A | 5/1988 | Linner et al. | |
| 4,968,325 A | 11/1990 | Black et al. | |
| 4,971,954 A | 11/1990 | Brodsky et al. | |
| 5,118,867 A | 6/1992 | Bahrmann et al. | |
| 5,284,655 A | 2/1994 | Bogdansky et al. | |
| 6,030,635 A | 2/2000 | Gertzman et al. | |
| 6,893,462 B2 * | 5/2005 | Buskirk et al. ............ 623/13.17 |
| 7,101,857 B2 | 9/2006 | Sung et al. | |
| 7,311,904 B2 | 12/2007 | Hariri | |
| 7,311,905 B2 | 12/2007 | Hariri | |
| 8,067,044 B2 | 11/2011 | Henry et al. | |
| 8,153,162 B2 | 4/2012 | Tseng et al. | |
| 8,323,701 B2 | 12/2012 | Daniel et al. | |
| 8,357,403 B2 | 1/2013 | Daniel et al. | |
| 8,372,439 B2 | 2/2013 | Daniel et al. | |
| 2001/0053839 A1 | 12/2001 | Noishiki et al. | |
| 2002/0019516 A1 | 2/2002 | Noff et al. | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2004/0048796 A1 * | 3/2004 | Hariri et al. .................... 514/12 |
| 2006/0140913 A1 | 6/2006 | Bhatia | |
| 2006/0210532 A1 | 9/2006 | Carmeliet et al. | |
| 2007/0021762 A1 | 1/2007 | Liu et al. | |
| 2007/0202189 A1 | 8/2007 | Ahlfors | |
| 2007/0248575 A1 | 10/2007 | Connor et al. | |
| 2007/0299043 A1 | 12/2007 | Hunter et al. | |
| 2008/0046095 A1 * | 2/2008 | Daniel ..................... 623/23.74 |
| 2008/0050347 A1 | 2/2008 | Ichim | |
| 2008/0069895 A1 * | 3/2008 | Liu et al. ..................... 424/583 |
| 2008/0131966 A1 | 6/2008 | Hariri | |
| 2008/0181967 A1 | 7/2008 | Liu et al. | |
| 2008/0233552 A1 | 9/2008 | Ma et al. | |
| 2009/0012629 A1 | 1/2009 | Yao et al. | |
| 2009/0142831 A1 | 6/2009 | Hariri | |
| 2009/0291891 A1 | 11/2009 | Neufeld | |
| 2010/0028849 A1 | 2/2010 | Shelby et al. | |
| 2010/0104539 A1 | 4/2010 | Daniel et al. | |
| 2010/0136114 A1 | 6/2010 | Mao | |
| 2010/0143312 A1 | 6/2010 | Hariri et al. | |
| 2010/0178297 A1 | 7/2010 | Carmeliet et al. | |

(Continued)

FOREIGN PATENT DOCUMENTS

| | | |
|---|---|---|
| EP | 0431479 A1 | 6/1991 |
| JP | H07-213597 | 8/1995 |

(Continued)

OTHER PUBLICATIONS

International Search Report and Written Opinion dated Feb. 8, 2013 in related PCT Application No. PCT/US2012/065672.
U.S. Appl. No. 13/984,842, filed Mar. 14, 2014, Morse et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.

(Continued)

*Primary Examiner* — Robert A Wax
*Assistant Examiner* — Danah Al-Awadi
(74) *Attorney, Agent, or Firm* — Foley & Lardner LLP (57) ABSTRACT

Described herein are tissue grafts produced by contacting dehydrated placental tissue grafts with a cross-linking agent. The tissue grafts described herein provide barrier and prevent the migration of a bioactive agent from the wound. Thus, the tissue grafts enhance wound healing while preventing the undesirable migration of a bioactive agent from the wound. Methods for making and using the cross-linked grafts are also described herein.

8 Claims, 2 Drawing Sheets

(56) References Cited

U.S. PATENT DOCUMENTS

| | | |
|---|---|---|
| 2010/0209408 A1 | 8/2010 | Stephen et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0083900 A1 | 4/2012 | Samaniego et al. |
| 2014/0017280 A1 | 1/2014 | Daniel et al. |
| 2014/0052247 A1 | 2/2014 | Daniel et al. |

FOREIGN PATENT DOCUMENTS

| | | |
|---|---|---|
| KR | 10/1991/0011272 | 8/1991 |
| KR | 10/1991/0011727 | 8/1991 |
| WO | WO-93/10722 | 6/1993 |
| WO | WO-01/08716 A1 | 2/2001 |
| WO | WO-2005/007835 A1 | 1/2005 |
| WO | WO-2005/017165 A1 | 2/2005 |
| WO | WO-2009/033160 A1 | 3/2009 |
| WO | WO-2009/048908 A1 | 4/2009 |
| WO | WO-2009/132186 A1 | 10/2009 |
| WO | WO-2010/029344 A2 | 3/2010 |
| WO | WO-2012/069559 A1 | 5/2012 |
| WO | WO-2012/112410 A2 | 8/2012 |
| WO | WO-2012/112417 A2 | 8/2012 |
| WO | WO-2012/112441 A1 | 8/2012 |

OTHER PUBLICATIONS

Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.

Koob et al., "Biological properties of dehydrated human amnion-chorion composite graft: implications for chronic wound healing", International Wound Healing, 2013, 10(5):493-500.

Mayfield et al., "Watertight closure of spinal dura mater: Technical note," J. Neurosurg., (1975), 43(5):639-640.

Tao, et al., "Implantation of amniotic membrane to reduce postlaminectomy epidurla adhesions," Eur. Spine. J., (2009), 18:1202-1212.

EP Search Report dated Jun. 24, 2015 for European Patent Application No. 12859455.3.

Kelly et al., "Disparate Effects of Similar Phenolic Phytochemicals as Inhibitors of Oxidative Damage to Cellular DNA", Mutation Res., vol. 485, pp. 309-318, (2001).

Lu. et al., "Molecular mechanisms and clinical applications of nordihydroguaiaretic acid (NDGA) and its derivatives: An update," Med. Sci. Monit., (2010), 16(5):RA93-RA100.

Moussy et al., "Transport characteristics of a novel local drug delivery system using nordihydroguaiaretic acid (NDGA)-polymerized collagen fibers," Biotechnology Progress, (2007), 23(4):990-994.

PCT International Preliminary Report on Patentability dated Nov. 28, 2014, for International Patent Application No. PCT/US2013/054319.

\* cited by examiner

CROSS-LINKED DEHYDRATED PLACENTAL TISSUE GRAFTS AND METHODS FOR MAKING AND USING THE SAME

CROSS-REFERENCE TO RELATED APPLICATION

This application claims the benefit under 35 U.S.C. 119(e) of U.S. Provisional Application No. 61/579,206, filed Dec. 22, 2011 which is incorporated by reference in its entirety into this application.

BACKGROUND

In wound healing applications, a drug or bioactive agent is typically applied to the wound in order enhance wound healing. Depending upon the bioactive agent, it is desirable to keep the agent localized in the wound such that it does not leave the wound and migrate to other body parts of the subject. This is particularly relevant when the bioactive agent is toxic when released systemically throughout the subject. Thus, it would be desirable to have a wound healing device that prevents the migration of bioactive agents administered to the wound.

SUMMARY

Described herein are tissue grafts produced by contacting dehydrated placental tissue grafts with a cross-linking agent. The tissue grafts described herein provide barrier and prevent the migration of a bioactive agent from the wound. Thus, the tissue grafts enhance wound healing while preventing the undesirable migration of a bioactive agent from the wound. Methods for making and using the cross-linked grafts are also described herein.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism.

The term "amnion membrane" as used herein includes amniotic tissue where the intermediate tissue layer has not been removed.

The term "amnion" as used herein includes amnion tissue where the intermediate tissue layer has been removed.

Titles or subtitles may be used in the specification for the convenience of a reader, which are not intended to influence the scope of the present invention. Additionally, some terms used in this specification are more specifically defined below.

I. Cross-Linked Tissue Grafts and Methods for Making Thereof

Described herein are tissue grafts derived from contacting a dehydrated placental tissue graft with a cross-linking agent. The tissue grafts described herein are composed of one or more placental components. The term "placental components" as used herein include any materials or tissues present in the placenta and the umbilical cord. In one aspect, placental components include, but are not limited to, amnion membrane, amnion, chorion, Wharton's jelly, placental disk, or any combination thereof.

Figure 1:
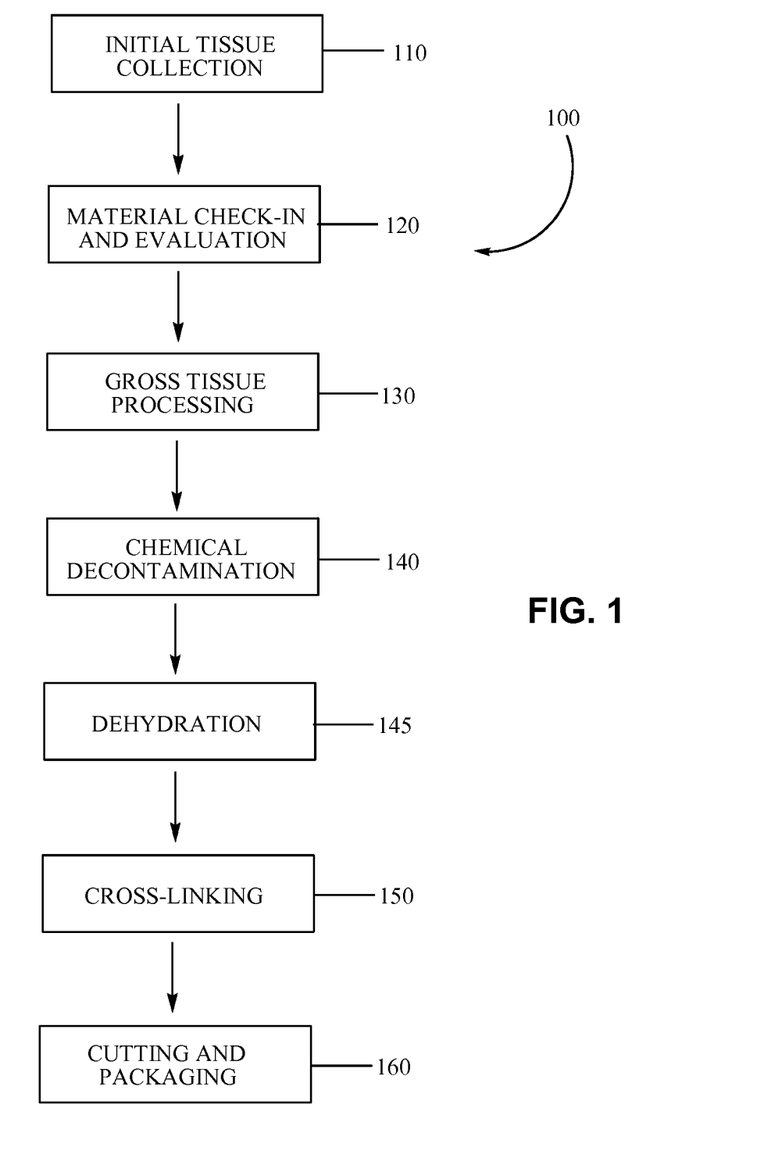
FIG. 1 is an overview flow chart of the process for making the tissue graft compositions described herein.

FIG. 1 depicts an exemplary, non-limiting overview (100) and certain aspects of the steps to harvest, process, and prepare placental tissues for use in the preparation of the tissue grafts described herein. More detailed descriptions and discussion regarding each individual step will follow. Initially, the placenta is collected (step 110). The material is preserved and transported in conventional tissue preservation manner to a suitable processing location or facility for check-in and evaluation (step 120). Gross processing, handling, and separation of the placental tissue then takes place (step 130). Acceptable tissue is then decontaminated (step 140). After decontamination, the placental tissue is dehydrated and (step 145), and the dehydrated tissue graft is subsequently contacted with a cross-linking agent (step 150). The cross-linked tissue graft can then be cut to a desirable size and subsequently packaged for future use (step 160). Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion or obtaining of results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-In and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to the ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

In one aspect, if the placenta is deemed acceptable for further processing, the amnion membrane, Wharton's jelly, and chorion are collectively dissected from the placenta. In this aspect, the amnion membrane, Wharton's jelly, and chorion are not separated from one, and this resulting placental tissue is further processed as discussed below.

In another aspect, the amnion membrane and chorion of the placenta can be carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion membrane can be separated from the chorion. The amnion membrane appears as a thin, opaque layer on the chorion.

The fibroblast layer is identified by gently contacting each side of the amnion membrane with a piece of sterile gauze or a cotton tipped applicator. The fibroblast layer will stick to the test material. The amnion membrane is placed into processing tray basement membrane layer down. Using a blunt instrument, a cell scraper or sterile gauze, any residual blood is also removed. This step must be done with adequate care, again, so as not to tear the amnion membrane. The cleaning of the amnion membrane is complete once the amnion membrane is smooth and opaque-white in appearance.

In certain aspects, the intermediate tissue layer is removed from the amnion membrane. This can be performed by peeling the intermediate tissue layer from the amnion membrane. Alternatively, the intermediate tissue layer can be removed from the amnion membrane by wiping the intermediate tissue layer with a gauze or other suitable wipe. The resulting amnion can be subsequently decontaminated using the process described below. The intermediate tissue layer does not require any additional processing and can be used as-is.

In certain aspects, the Wharton's jelly can optionally be isolated using the following procedure. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion membrane is removed from the Wharton's jelly by cutting the amnion membrane. After removing the amnion membrane from the Wharton's jelly, the Wharton's jelly can be cut into strips. In one aspect, the strips are approximately 1-4 cm by 10-30 cm with an approximate thickness of 1.25 cm; however, other thicknesses are possible depending on application.

Chemical Decontamination (Step 140)

Any of the placental tissues discussed herein can be chemically decontaminated using the techniques described below. In one aspect, the placental tissue is decontaminated at room temperature. In one aspect, the amnion membrane produced in step 130 can be placed into a sterile Nalgene jar for the next step. In one aspect, the following procedure can be used to clean the amnion membrane. Each Nalgene jar is aseptically filled with 18% saline hypertonic solution and sealed (or sealed with a top). The jar is then placed on a rocker platform and agitated for between 30 and 90 minutes, which further cleans the amnion membrane of contaminants. If the rocker platform was not in the critical environment (e.g., the manufacturing hood), the Nalgene jar is returned to the controlled/sterile environment and opened. Using sterile forceps or by aseptically decanting the contents, the amnion membrane is gently removed from the Nalgene jar containing the 18% hyperisotonic saline solution and placed into an empty Nalgene jar. This empty Nalgene jar with the amnion membrane is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion membrane. This jar or container containing the amnion membrane and antibiotics is then sealed or closed and placed on a rocker platform and agitated for, preferably, between 60 and 90 minutes. Such rocking or agitation of the amnion membrane within the antibiotic solution further cleans the tissue of contaminants and bacteria. Optionally, the amnion membrane can be washed with a detergent. In one aspect, the amnion membrane can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion membrane and antibiotics is then returned to the critical/sterile environment and opened. Using sterile forceps, the amnion membrane is gently removed from the jar or container and placed in a sterile basin containing sterile water or normal saline (0.9% saline solution). The amnion membrane is allowed to soak in place in the sterile water/normal saline solution for at least 10 to 15 minutes. The amnion membrane may be slightly agitated to facilitate removal of the antibiotic solution and any other contaminants from the tissue. After at least 10 to 15 minutes, the amnion membrane is ready to be dehydrated and processed further.

In the case when the chorion is to be used, the following exemplary procedure can be used. After separation of the chorion from the amnion membrane and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the amnion membrane. The container is sealed and agitated without heat 15 minutes to 120 minutes hours. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

In the case of the decontamination of Wharton's jelly, it can be transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) 18% NaCl is added. The container is sealed and placed on a rocker plate and agitated for 60 to 90 minutes.

In one aspect, after the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours. The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After the incubation, the jar is returned to the sterile field. The Wharton's jelly should have a cream white visual appearance with no evidence of brownish discoloration. The tissue is ready for further processing.

In other aspects, when the placental tissue is amnion membrane, Wharton's jelly, and chorion that has not been separated, the placental tissue can be decontaminated using any of the techniques and solutions described above (e.g., antibiotic solutions, detergents such as Triton X, etc.).

In certain aspects, it is desirable to remove epithelium layer present on the amnion membrane after chemical decontamination. In one aspect, the epithelium layer present on the amnion membrane is substantially removed in order to expose the basement layer of the amnion membrane. The term "substantially removed" with respect to the amount of epithelium removed is defined herein as removing greater than 50%, greater than 60%, greater than 70%, greater than 80%, greater than 90%, greater than 95%, or greater than 99% of the epithelial cells from the amnion. The presence or absence of epithelial cells remaining on the amnion membrane can be evaluated using techniques known in the art. For example, after removal of the epithelial cell layer, a representative tissue sample from the processing lot is placed onto a standard microscope examination slide. The tissue sample is then stained using Eosin Y Stain and evaluated. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the tissue has been dehydrated as described in the next section. For example, a representative sample graft is removed for microscopic analysis. The tissue sample is place onto a standard slide and 100 µl of Eosin Y stain is applied to the sample and allowed to set. The tissue sample is then examined under magnification. Cellular material will stain dark indicating the presence of cells. If no stained cells are present, de-epithelization has been achieved.

Dehydration (Step 145)

One or more placental tissues prepared above can be dehydrated to produce dehydrated placental tissue grafts. In the case when two or more placental tissues are used, the tissue graft is a laminate. For example, a laminate composed of amnion, amnion membrane, chorion, Wharton's jelly, or any combination thereof can be produced. In one aspect, the tissue graft is an amnion/chorion laminate. In another aspect, the tissue has at least two layers of chorion, at least two layers of amnion, or at least one layer of chorion and amnion. In a further aspect, the placental tissue graft has a plurality chorion and/or amnion membranes laminated to one another. Techniques for producing laminated tissue grafts are know in the art.

In one aspect, the tissue graft is dehydrated by chemical dehydration followed by freeze-drying. In one aspect, the chemical dehydration step is performed by contacting the placental tissue with a polar organic solvent for a sufficient time and amount in order to substantially (i.e., greater than 90%, greater than 95%, or greater than 99%) or completely remove residual water present in the placental tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the placental tissue can be freeze-dried directly as discussed below.

After chemical dehydration, the placental tissue graft is freeze-dried in order to remove any residual water and polar organic solvent. In one aspect, the placental tissue is placed in a freeze-dryer, and the placental tissue is lyophilized between −50° C. to −80° C. In another aspect, the placental tissue is placed in a freeze-dryer such that it is hanging in the freeze-dryer. In other aspects, the placental tissue is placed on a substrate that can facilitate free-drying. Examples of such substrates include, but are not limited to, a pan, bowl, screen, or a frame. In one aspect, one or more placental tissues can optionally be laid on a suitable drying fixture prior to freeze-drying. For example, at least two layers of hydrated chorion, at least two layers of hydrated amnion, or at least one layer of hydrated chorion and hydrated amnion can be applied to the drying fixture. In other aspects, the placental tissue composed of amnion membrane, Wharton's jelly, and chorion that has not been separated can be laid on top of the drying fixture, where one or more additional placental tissues such as amnion membrane and/or chorion can optionally be applied on top of the tissue.

The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

In one aspect, the receiving surface of the drying fixture can have grooves that define the product spaces, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another aspect, instead of having grooves to define the product spaces, the drying fixture has raised ridges or blades.

In certain aspects, the drying fixture can include a slightly raised or indented texture in the form of text, logo, name, or similar design. This textured text, logo, name, or design can be customized or private labeled depending upon the company that will be selling the graft or depending upon the desired attributes requested by the end user (e.g., surgeon). When dried, the tissue will mold itself around the raised texture or into the indented texture, essentially providing a label within the tissue itself. Preferably, the texture/label can be read or viewed on the placental tissue in only one orientation so that, after dehydration, an end user (e.g., a surgeon) of the dried tissue will be able to identify the top and bottom of the placental tissue. In other aspects, a stamp can be imprinted on the placental tissue graft after freeze-drying in order to differentiate the sides of the graft.

Once the placental tissue(s) is placed on the drying fixture, the drying fixture is placed in the freeze-dryer. The use of the freeze-dryer to dehydrate the placental tissue grafts can be more efficient and thorough compared to other techniques such as thermal dehydration. In general, it is desirable to avoid ice crystal formation in the placental tissue grafts as this may damage the extracellular matrix in the tissue graft. By chemically dehydrating the placental tissue prior to freeze-drying, this problem can be avoided.

In another aspect, the dehydration step involves applying heat to the placental tissue. In one aspect, the placental component is laid on a suitable drying fixture as discussed above, and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 and 120 minutes, although approximately 45 minutes at a temperature of approximately 45 degrees Celcius appears to be ideal to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Cross-Linking (Step 150)

Figure 2:
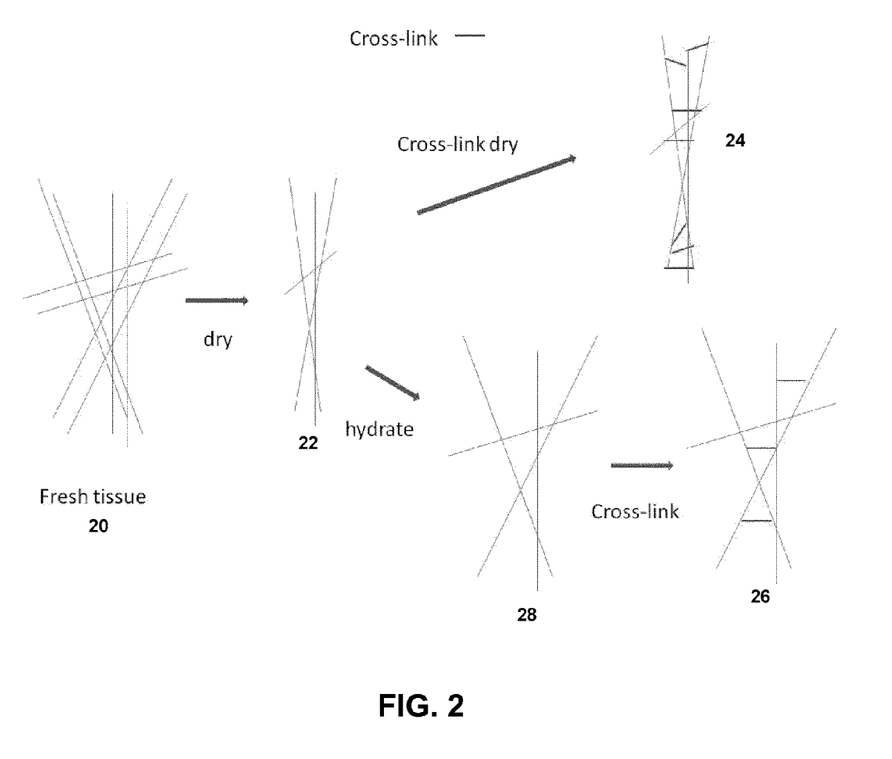
FIG. 2 shows the cross-linking of dehydrated and hydrated placental tissue.

After the placental tissue graft has been dehydrated, the graft is contacted with a cross-linking agent. Not wishing to be bound by theory, cross-linking the dehydrated tissue graft produces a graft having increased density and reduced pore size compared to cross-linking a hydrated tissue graft. This is depicted in FIG. 2, where placental tissue 20 is dehydrated to produce dehydrated tissue graft 22. Cross-linking of the dehydrated tissue graft 22 produces tissue graft 24, which is a more compact, dense, and less porous compared to tissue graft 26 that is cross-linked from hydrated tissue graft 28. The relevance of producing a dense tissue graft with reduced porosity is discussed below.

The dehydrated tissue graft can be contacted with the cross-linking agent using techniques known in the art. In one aspect, the dehydrated tissue graft is placed directly into a solution of cross-linking agent. Not wishing to be bound by theory, cross-linking proceeds from the surface of the tissue graft inward towards the center of the graft. The surface of the tissue is cross-linked immediately upon immersion, which prevents the tissue from swelling when taking up the solution. As the cross-linker permeates the graft, covalent cross-links are formed before swelling of the tissue can take place, thereby further limiting swelling.

In general, the cross-linking agent is nontoxic and non-immunogenic. In certain aspects, the placental tissue can be treated with two or more different cross-linking agents. The conditions for treating the placental tissue can vary. In one aspect, the placental tissue can be placed in a container holding an aqueous solution of the cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. In another aspect, the placental tissue is treated with the cross-linking agent for 1 to 2 seconds up to 60 minutes. In a further aspect, the placental tissue is treated with the cross-linking agent at room temperature up to 50° C.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, epoxide groups, hydrazide groups, and aldehyde groups. In one aspect, the cross-linker can be a dialdehydes such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy]succinimide ester, p-azidophenyl glyoxal monohydrate, bis-[beta-(4-azidosalicylamido)ethyl]disulfide, bis-[sulfosuccinimidyl]suberate, dithiobis[succinimidyl] propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as cross-linking agent include, but are not limited to, D-ribose, glycerone, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof. Thus, in one aspect, an amnion membrane or a chorion membrane includes at least one cross-linker covalently attached to the membrane. In another aspect, a tissue graft includes an amnion membrane and a chorion membrane, wherein the amnion membrane and chorion membrane are covalently attached to one another via a cross-linker.

The following procedure provides an exemplary method for treating a dehydrated amnion/chorion tissue graft with a cross-linking agent. The tissue graft is placed in a Nalgene jar containing a cross-linking agent, preferably 0.05 to 1 M D-ribose, preferably 0.2 M (3.01%) D-ribose, for 1 to 60 minutes, preferably 5 minutes. After the incubation, the tissue graft is removed from the solution. The cross-linked tissue graft can then be rinsed with water or another appropriate solvent to remove any excess cross-linking agent and subsequently dehydrated using the techniques described above.

In certain aspects, it may be desirable to cross-link the placental tissue used to make the graft prior to dehydration step 145. For example, amnion and chorion can be independently contacted with a cross-linking agent prior to lamination, dehydration, and subsequent cross-linking. In another aspect, an amnion/chorion graft can be produced and cross-linked prior to the dehydration step 145 and subsequent cross-linking. Any of the cross-linking agents and techniques described above can be used in these embodiments.

Cutting & Packaging (Step 160)

Once the tissue graft has been adequately dehydrated after cross-linking, the tissue graft is then ready to be cut into specific product sizes and appropriately packages for storage, terminal sterilization, and later surgical use. The number of grafts to be produced is estimated based on the size and shape of the tissue on the drying fixture(s). An appropriate number of pouches, one for each tissue graft, are then also introduced into the sterile/controlled environment.

In one aspect, if a drying fixture is used and has grooves, then the following exemplary procedure is followed for cutting the tissue into product sizes. If the drying fixture is configured in a grid pattern, a #20 or similar straight or rolling blade is used to cut along each groove line in parallel. Then, all lines in the perpendicular direction are cut. Alternatively, if the drying fixture has raised edges or blades, then the following procedure is followed for cutting the tissue into product sizes. A sterile roller is used to roll across the drying fixture. Sufficient pressure must be applied so that the dehydrated tissue is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate graft.

Each tissue graft is then given a final inspection to confirm that there are no tears or holes, that the product size (as cut) is within approximately 1 millimeter (plus or minus) of the specified size for that particular graft, that there are no noticeable blemishes or discoloration of the tissue, and that the textured logo or wording is readable and viewable through the "inner" pouch. The final tissue grafts can be stored at room temperature for extended periods of time.

II. Applications for Cross-Linked Tissue Grafts

The grafts described herein can be used in numerous medical applications involving wound healing in a subject. As discussed above, the cross-linked tissue grafts described herein are more compact and dense compared to hydrated placental tissue that has been cross-linked. Additionally, the porosity of the tissue grafts described herein is lower when compared to cross-linked, hydrated tissue grafts. The tissue grafts described herein are useful in wound healing applications where it is desirable to keep a bioactive agent localized in the wound so that the wound heals quicker. Additionally, if the bioactive agent is toxic when released systemically throughout the subject, the tissue grafts described herein can provide an effective, impermeable barrier that prevents the bioactive agent from migrating from the wound.

The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the grafts described herein can function as a tissue regeneration template that delivers essential wound healing factors, extracellular matrix proteins and inflammatory mediators to help reduce inflammation, enhance healing, and reduces scar tissue formation.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the graft protects the spinal dura from post-surgical trauma from the surrounding surgical site. For example, the grafts can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue graft can be applied directly to the spinal dura, the surrounding region of the spine to include nerve roots, or a combination thereof. Due to the unique structure of vertebrae, the tissue graft can be cut into any shape or dimension so that it can be placed and affixed at the appropriate position in the subject. For example, when the tissue graft is used for bi-lateral coverage, membranes in the shape of a rectangle allow the tissue graft to fit around the posterior spinal process, which minimizes lateral movement. In addition to minimizing lateral movement, the tissue graft can also provide proximal and distal barrier coverage where the spinal lamina has been removed for exposure to the affected area. In one aspect, to ensure proper placement, the graft can be embossed on the exposed basement membrane of the graft to ensure proper placement of the graft in the subject. In particular, proper graft placement will ensure that the basement membrane of the graft is in direct contact with the spinal dura or surrounding region. For example, proper membrane placement and orientation is important when applying the material in spinal applications where a posterior or anterior approach is utilized.

The grafts are useful in preventing or reducing scar formation that can result from a variety of surgical procedures associated with the spine. The grafts can be used after any procedure in the neck, mid-back, or lower back. Depending upon the application, the epithelium of the amnion membrane can be substantially removed. For example, in posterior procedures such as a laminectomy or discectomy, the epithelium layer is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures. Thus, the grafts described herein provide an unmet need in these procedures.

In other aspects, the epithelial cell layer is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the grafts provide additional protection to the vertebral surgical site by maintaining separation from the peritoneum, larger vessels, and abdominal musculature. The membrane serves as a reduced friction anatomical barrier against adhesions and scaring. For example, the grafts can prevent scar tissue binding major blood vessels to the spine. This is a common problem with post-spinal surgery, which requires a second surgical procedure to address this.

In another aspect, the tissue grafts are useful in dental applications. For example, the grafts can be used around dental implants or in the treatment of advanced gingival recession defect. In another aspect, the grafts can be used in guided tissue regeneration.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts described herein can be used to wrap tendon repairs to prevent scar formation on the healing tendon. They can also provide a protective, enclosed environment for the repair to progress successfully. The tissue grafts can be used as an off-the-shelf tendon and ligament to replace the need to purchase an allograft or perform tendon or ligament transfer.

In other aspects, the tissue grafts described herein can be used in the reinforcement of rotator cuffs. Some rotator cuff tears are large enough that they require a reinforcement matrix to support the repair due to lack of viable native tissue. The tissue grafts described herein can be used as a matrix to reinforce a repair. In one aspect, the tissue grafts described herein can be used to repair knee cartilage. For example, the tissue grafts can be used as a barrier to hold cell cultured chondrocytes or other pro-cartilage regeneration matrix inside a chondral defect. In this aspect, the tissue graft would be utilized as a flap to close the defect and hold the matrix in place.

In one aspect, the tissue grafts can be used to repair peripheral nerves. The tissue graft can be used as a wrap on nerve repairs to prevent scar formation onto the healing nerve. The tissue graft can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts can be laid on the nerves to keep them from scarring and possibly damaging the nerves.

In other aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In one aspect, the tissue grafts described herein can be used in applications where bone grafts are typically used. Such applications include, but are not limited to, interbody fusion, intertransverse process fusion, fresh fractures, non-union fractures, joint reconstruction, tibial metaphysis, foot and ankle fusions, primary and secondary alveolar ridge augmentations, sinus elevations, socket augmentation, site preservation, and periodontal intrabony defects. For example, the tissue grafts described can be useful in facilitating the healing of a bone fracture where one or more bone grafts are applied to the fracture. Here, the tissue grafts described herein can be applied directly to the fracture after the bone graft has been applied in order to prevent migration of the bone graft from the fracture, which ultimately enhances the healing of the fracture. For example, the bone graft INFUSE® manufactured by Medtonic can be applied directly to the bone of a subject followed by the application of the tissue graft to the bone. In this aspect, the tissue graft enhances wound healing as well as reduce or prevent the likelihood of undesirable side-effects that may be caused by INFUSE® being released systemically throughout the subject.

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue graft can be used as an anti-adhesion barrier after removal of ovarian cyst or aid in the repair of vaginal wall erosion.

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels).

The tissue grafts described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts can be used in ophthalmological applications (e.g., on-lay grafts ocular surface repair) or urological applications (e.g., facilitate closure of the vas deferens during vasectomy reversal or facilitate closure of the vas deferens resulting from trauma).

Depending upon the application of the graft, the graft can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

Although the tissue grafts described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A laminated placental tissue graft comprising multiple dehydrated layers, said multiple dehydrated layers comprising dehydrated amnion and chorion layers wherein at least one of the amnion layers comprises a fibroblast cell layer and/or an epithelial cell layer, and one or more layers of amnion or chorion, wherein at least one dehydrated layer has been treated with a cross-linking agent and further wherein the placental tissue graft is laminated together and the cross-linking agent comprises a sugar, a dialdehyde, an epoxide, a hydrazide, or carbodiimide.

2. The graft of claim 1, wherein the placental tissue graft comprises at least two layers of chorion, at least two layers of amnion, or at least one layer of chorion and at least one layer of amnion.

3. The graft of claim 1, wherein the placental tissue graft comprises a plurality of chorion and/or amnion membranes laminated to one another.

4. The graft of claim 1, wherein the placental tissue graft is chemically dehydrated or thermally dehydrated.

5. The graft of claim 1, wherein the sugar comprises D-ribose, glycerose, altrose, talose, glucose, lyxose, mannose, xylose, gulose, arabinose, idose, allose, galactose, maltose, lactose, sucrose, cellibiose, gentibiose, melibiose, turanose, trehalose, isomaltose, or any combinations thereof.

6. A wound dressing comprising the tissue graft of claim 1.

7. The graft of claim 1, wherein at least one layer of amnion comprises a fibroblast cell layer and the epithelial cell layer is substantially removed.

8. The graft of claim 1, wherein at least one layer of amnion comprises an epithelial cell layer.

* * * * *